(12) United States Patent
Inoue et al.

(10) Patent No.: US 9,775,503 B2
(45) Date of Patent: Oct. 3, 2017

(54) ENDOSCOPE REPROCESSOR

(71) Applicant: OLYMPUS CORPORATION, Tokyo (JP)

(72) Inventors: Ryo Inoue, Hino (JP); Atsushi Kinoshima, Higashiyamato (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/385,075

(22) Filed: Dec. 20, 2016

(65) Prior Publication Data

US 2017/0100026 A1    Apr. 13, 2017

Related U.S. Application Data

(63) Continuation of application No. PCT/JP2016/060172, filed on Mar. 29, 2016.

(30) Foreign Application Priority Data

Aug. 12, 2015  (JP) ................. 2015-159529

(51) Int. Cl.
*A61B 1/12*     (2006.01)
*B08B 9/032*    (2006.01)
*B08B 3/08*     (2006.01)

(52) U.S. Cl.
CPC ............... *A61B 1/123* (2013.01); *B08B 3/08* (2013.01); *B08B 9/0321* (2013.01)

(58) Field of Classification Search
CPC .......... A61B 1/123; B08B 3/08; B08B 9/0321
See application file for complete search history.

(56) References Cited

U.S. PATENT DOCUMENTS

| | | | |
|---|---|---|---|
| 7,479,257 B2 * | 1/2009 | Nguyen ................. | A61B 1/123 422/119 |
| 2007/0048183 A1 * | 3/2007 | Nguyen ................. | A61B 1/123 422/62 |
| 2010/0004510 A1 * | 1/2010 | Kuroshima ............ | A61B 1/012 600/158 |
| 2013/0125934 A1 | 5/2013 | Komiya et al. | |

(Continued)

FOREIGN PATENT DOCUMENTS

| | | |
|---|---|---|
| JP | 2011-092425 A | 12/2011 |
| JP | 2010-051574 A | 11/2013 |
| WO | WO2013011724 A1 | 1/2013 |

*Primary Examiner* — Michael Barr
*Assistant Examiner* — Benjamin L Osterhout
(74) *Attorney, Agent, or Firm* — Scully, Scott, Murphy & Presser, P.C.

(57) ABSTRACT

An endoscope reprocessor includes: a medicinal solution storage portion configured to store a medicinal solution; a sampling tube including a first end portion opened inside the medicinal solution storage portion, and a second end portion opened outside the medicinal solution storage portion; a first chamber, inside which the second end portion of the sampling tube is opened; a second chamber where an opening portion and a communication port communicated with the first chamber are formed; a constricted portion configured to connect the first chamber and the communication port; a first advancing/retreating portion configured to advance and retreat between a first position to block the constricted portion and a second position to open the constricted portion inside the first chamber.

8 Claims, 13 Drawing Sheets

(56) References Cited

U.S. PATENT DOCUMENTS

2016/0128554 A1\* 5/2016 Takada ................... A61B 1/123
                                                    134/166 C
2017/0082529 A1\* 3/2017 Onishi ..................... A61B 1/12
2017/0087604 A1\* 3/2017 Kosugi ................ B08B 9/0325

\* cited by examiner

ENDOSCOPE REPROCESSOR

CROSS REFERENCE TO RELATED APPLICATION

This application is a continuation application of PCT/JP2016/060172 filed on Mar. 29, 2016 and claims benefit of Japanese Application No. 2015-159529 filed in Japan on Aug. 12, 2015, the entire contents of which are incorporated herein by this reference.

BACKGROUND OF THE INVENTION

1. Field of the Invention

The present invention relates to an endoscope reprocessor including a medicinal solution storage portion configured to store a medicinal solution.

2. Description of the Related Art

An endoscope used in a medical field is subjected to reprocessing treatment using a medicinal solution such as cleaning treatment and disinfecting treatment after use. In addition, an endoscope reprocessor which automatically performs the reprocessing treatment of an endoscope is known. The endoscope reprocessor includes a medicinal solution storage portion configured to store a medicinal solution.

In the case of executing the reprocessing treatment by an endoscope reprocessor, a medicinal effect confirmation test that confirms whether or not the medicinal solution stored in the medicinal solution storage portion has a predetermined medicinal effect is carried out. For example, Japanese Patent Application Laid-Open Publication No. 2011-92425 discloses an endoscope reprocessor including a medicinal solution sampling portion that samples a medicinal solution stored inside a medicinal solution storage portion in order to carry out a medicinal effect confirmation test.

SUMMARY OF THE INVENTION

An endoscope reprocessor according to one aspect of the present invention includes: a medicinal solution storage portion configured to store a medicinal solution; a sampling tube including a first end portion opened at or below a predetermined water level inside the medicinal solution storage portion, and a second end portion opened at a position higher than the predetermined water level outside the medicinal solution storage portion; a first chamber, inside which the second end portion of the sampling tube is opened; a second chamber where an opening portion and a communication port communicated with the first chamber are formed; a constricted portion configured to connect the first chamber and the communication port and provided with an inner diameter smaller than an inner diameter of the first chamber; a first advancing/retreating portion configured to advance and retreat between a first position to block the constricted portion and a second position to open the constricted portion farther away from the constricted portion than the first position, inside the first chamber; and a retention portion arranged at the constricted portion or the first advancing/retreating portion and configured to retain the first advancing/retreating portion at the first position.

DETAILED DESCRIPTION OF THE PREFERRED EMBODIMENT(S)

Hereinafter, preferred embodiments of the present invention will be described with reference to the drawings. Note that, in the individual diagrams used in the following description, a scale is made different for each component in order to turn the individual components to such sizes that the components can be recognized on the drawings, and the present invention is not limited only to quantities of the components, shapes of the components, ratios of the sizes of the components, and relative positional relationships of the individual components described in the diagrams.

First Embodiment

Figure 1:
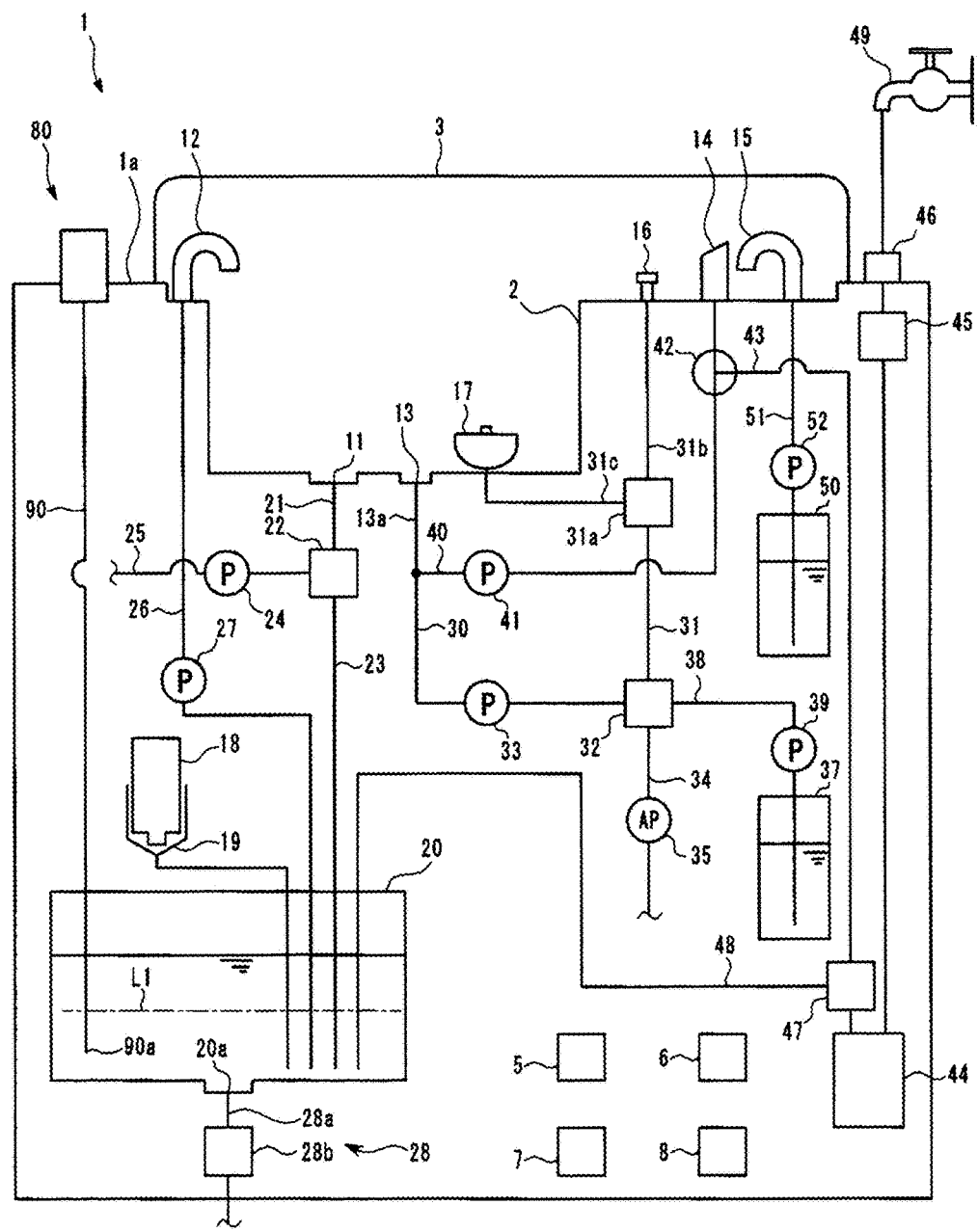
FIG. 1 is a diagram illustrating a configuration of an endoscope reprocessor of a first embodiment.

Hereinafter, one example of the embodiment of the present invention will be described. An endoscope reprocessor 1 illustrated in FIG. 1 is a device configured to execute reprocessing treatment to an endoscope. The reprocessing treatment here is not limited in particular, and may be any one of rinsing treatment with water, cleaning treatment of removing smudges such as organic matters, disinfecting treatment of disabling predetermined microorganisms, sterilization treatment of eliminating or annihilating all the microorganisms, or the combination.

Note that, in the following description, an upper part indicates a position farther away from a ground surface in contrast with a comparison object, and a lower part indicates a position closer to the ground surface in contrast with the comparison object. In addition, height in the following description indicates a height relation along a gravity direction.

The endoscope reprocessor 1 includes a control portion 5, a power supply portion 6, a treatment tank 2, a medicinal solution storage portion 20, and a medicinal solution sampling portion 80.

The control portion 5 can be configured including an arithmetic unit (CPU), a storage device (RAM), an auxiliary storage device, an input/output device, a power controller and the like, and has a configuration to control operations of individual portions configuring the endoscope reprocessor 1 based on a predetermined program. The operations of the individual configurations included in the endoscope reprocessor 1 in the following description are controlled by the control portion 5 even in the case of no description in particular.

The power supply portion 6 supplies power to the individual portions of the endoscope reprocessor 1. The power supply portion 6 distributes the power obtained from outside such as commercial power supply to the individual portions. Note that the power supply portion 6 may include a power generator or a battery.

The treatment tank 2 is in a recessed shape including an opening portion, and is capable of storing liquid inside. Inside the treatment tank 2, an endoscope not shown in the figure can be arranged. In the present embodiment, as one example, on an upper part of the treatment tank 2, a lid 3 that opens and closes the opening portion of the treatment tank 2 is provided. In the case of executing the reprocessing treatment to the endoscope inside the treatment tank 2, the opening portion of the treatment tank 2 is closed by the lid 3.

The treatment tank 2 includes a medicinal solution nozzle 12, a drainage port 11, a circulation port 13, a circulation nozzle 14, a cleaning solution nozzle 15, an endoscope connection portion 16, and an accessory case 17.

The medicinal solution nozzle 12 is an opening portion communicated with the medicinal solution storage portion 20 through a medicinal solution conduit 26. The medicinal solution storage portion 20 stores a medicinal solution. The medicinal solution conduit 26 includes a medicinal solution pump 27. By operating the medicinal solution pump 27, the medicinal solution inside the medicinal solution storage portion 20 is transferred into the treatment tank 2 through the medicinal solution conduit 26 and the medicinal solution nozzle 12.

While a kind of the medicinal solution stored in the medicinal solution storage portion 20 is not limited in particular, in the present embodiment, as one example, the medicinal solution is a disinfecting solution such as peracetic acid used in the disinfecting treatment. However, the present invention is not limited to the disinfecting solution, and as the medicinal solution, a cleaning solution used in the cleaning treatment and a highly volatile solution used in drying or the like can be appropriately selected according to a purpose.

In addition, in the present embodiment, as one example, the medicinal solution is the one for which a stock solution of the medicinal solution supplied from a medicinal solution bottle 18 is diluted with water by a predetermined ratio. The medicinal solution storage portion 20 of the present embodiment is communicated with a bottle connection portion 19 that introduces the stock solution of the medicinal solution supplied from the medicinal solution bottle 18 into the medicinal solution storage portion 20, and a dilution conduit 48 that introduces the water for dilution into the medicinal solution storage portion 20. By connecting the medicinal solution bottle 18 to the bottle connection portion 19, the stock solution of the medicinal solution is introduced into the medicinal solution storage portion 20. A configuration of introducing the water from the dilution conduit 48 into the medicinal solution storage portion 20 will be described later.

Note that, the endoscope reprocessor 1 may not include a configuration of diluting the medicinal solution with the water or the like. In addition, in the case that a plurality of kinds of the stock solutions are mixed and used for the medicinal solution, the bottle connection portion 19 can be connected to the plurality of medicinal solution bottles 18.

In addition, in the present embodiment, as one example, the medicinal solution is reusable in the case that a concentration is within a predetermined range of having a medicinal effect. The medicinal solution storage portion 20 serves also as a medicinal solution collection portion that collects the medicinal solution transferred from the inside of the medicinal solution storage portion 20 into the treatment tank 2 and stores the medicinal solution again.

In addition, at the medicinal solution storage portion 20, a drainage portion 28 is disposed. The drainage portion 28 discharges a liquid such as the medicinal solution or the water from the inside of the medicinal solution storage portion 20. The drainage portion 28 may be configured to discharge the liquid from the inside of the medicinal solution storage portion 20 by gravity, or configured to forcibly discharge the liquid from the inside of the medicinal solution storage portion 20 by a pump.

In the present embodiment, as one example, the drainage portion 28 includes a drain conduit 28a communicated with a drainage port 20a provided on a bottom surface of the medicinal solution storage portion 20 or near the bottom surface, and a drain valve 28b configured to open and close the drain conduit 28a. The drain valve 28b may be a solenoid valve controlled to be opened and closed by the control portion 5, or may be a cock opened and closed by a manual operation of a user.

Note that a route of discharging the liquid from the inside of the medicinal solution storage portion 20 is not limited only to the drain conduit. For example, by starting the operation of the medicinal solution pump 27, the liquid can be discharged from the inside of the medicinal solution storage portion 20 into the treatment tank 2 through the medicinal solution conduit 26 and the medicinal solution nozzle 12. In this case, the endoscope reprocessor 1 may not include the drainage port 20a, the drain conduit 28a and the drain valve 28b illustrated in FIG. 1.

In addition, inside the medicinal solution storage portion 20, a first end portion 90a of a sampling tube 90 is opened. The sampling tube 90 is included in a configuration of the medicinal solution sampling portion 80. The configuration of the medicinal solution sampling portion 80 will be described later.

The drainage port 11 is an opening portion provided on a lowest part inside the treatment tank 2. The drainage port 11 is connected to a discharge conduit 21. The discharge conduit 21 communicates the drainage port 11 and a switching valve 22. To the switching valve 22, a collection conduit 23 and a disposal conduit 25 are connected. The switching valve 22 can be switched to a state of blocking the discharge conduit 21, a state of communicating the discharge conduit 21 and the collection conduit 23, or a state of communicating the discharge conduit 21 and the disposal conduit 25.

The collection conduit 23 communicates the medicinal solution storage portion 20 and the switching valve 22. In addition, the disposal conduit 25 is provided with a discharge pump 24. The disposal conduit 25 is connected to drainage equipment for accepting the liquid discharged from the endoscope reprocessor 1.

When the switching valve 22 is turned to a closed state, the liquid can be stored inside the treatment tank 2. In addition, while the medicinal solution is stored inside the treatment tank 2, when the switching valve 22 is turned to the state of communicating the discharge conduit 21 and the collection conduit 23, the medicinal solution is transferred from the treatment tank 2 to the medicinal solution storage portion 20. In addition, when the switching valve 22 is turned to the state of communicating the discharge conduit 21 and the disposal conduit 25 and the operation of the discharge pump 24 is started, the liquid inside the treatment tank 2 is sent out through the disposal conduit 25 to the drainage equipment.

The circulation port 13 is an opening portion provided near the bottom surface of the treatment tank 2. The circulation port 13 is communicated with a circulation conduit 13a. The circulation conduit 13a is branched into two conduits which are an endoscope circulation conduit 30 and a treatment tank circulation conduit 40.

The endoscope circulation conduit 30 communicates the circulation conduit 13a and a channel valve 32 described later. The endoscope circulation conduit 30 is provided with a circulation pump 33. The circulation pump 33 is operated to transfer a fluid inside the endoscope circulation conduit 30 toward the channel valve 32.

To the channel valve 32, other than the above-described endoscope circulation conduit 30, an intake conduit 34, an alcohol conduit 38 and a send-out conduit 31 are connected. The channel valve 32 selectively communicates one of the endoscope circulation conduit 30, the intake conduit 34 and the alcohol conduit 38 to the send-out conduit 31.

For the intake conduit 34, one end portion is opened to atmospheric air, and the other end portion is connected to the channel valve 32. Note that, though not shown in the figure, one end portion of the intake conduit 34 is provided with a filter that filters a passing gas. An air pump 35 is provided in the intake conduit 34, and is operated to transfer the gas inside the intake conduit 34 toward the channel valve 32.

The alcohol conduit 38 communicates an alcohol tank 37 that stores alcohol and the channel valve 32. An example of the alcohol stored inside the alcohol tank 37 is ethanol. An alcohol concentration can be appropriately selected. An alcohol pump 39 is provided in the alcohol conduit 38, and is operated to transfer the alcohol inside the alcohol tank 37 toward the channel valve 32.

In the case that the liquid is stored inside the treatment tank 2, when the channel valve 32 is turned to the state of communicating the send-out conduit 31 and the endoscope circulation conduit 30 and the operation of the circulation pump 33 is started, the liquid inside the treatment tank 2 is sent into the send-out conduit 31 through the circulation port 13, the circulation conduit 13a and the endoscope circulation conduit 30.

In addition, when the channel valve 32 is turned to the state of communicating the send-out conduit 31 and the intake conduit 34 and the operation of the air pump 35 is started, air is sent into the send-out conduit 31. In addition, when the channel valve 32 is turned to the state of communicating the send-out conduit 31 and the alcohol conduit 38 and the operation of the alcohol pump 39 is started, the alcohol inside the alcohol tank 37 is sent into the send-out conduit 31.

The send-out conduit 31 is branched into an endoscope connection conduit 31b and a case connection conduit 31c. The endoscope connection conduit 31b is connected to the endoscope connection portion 16. In addition, the case connection conduit 31c is connected to the accessory case 17.

In addition, the send-out conduit 31 is provided with a flow channel switching portion 31a. The flow channel switching portion 31a can switch which of the endoscope connection conduit 31b and the case connection conduit 31c the fluid sent into the send-out conduit 31 from the channel valve 32 is to be made to flow to. Note that control may be performed to make a pressure on a side of the endoscope connection conduit 31b be constant upon switching.

The endoscope connection portion 16 is connected to a pipe sleeve provided in the endoscope through an endoscope tube not shown in the figure. In addition, the accessory case 17 is a basket-like member that accommodates accessories not shown in the figure of the endoscope. Therefore, the fluid sent into the send-out conduit 31 from the channel valve 32 is introduced into the pipe sleeve of the endoscope or into the accessory case 17.

The treatment tank circulation conduit 40 communicates the circulation conduit 13a and the circulation nozzle 14. The circulation nozzle 14 is an opening portion provided inside the treatment tank 2. The treatment tank circulation conduit 40 is provided with a liquid flow pump 41.

In addition, between the liquid flow pump 41 of the treatment tank circulation conduit 40 and the circulation nozzle 14, a three-way valve 42 is provided. To the three-way valve 42, a water supply conduit 43 is connected. The three-way valve 42 can be switched to the state of communicating the circulation nozzle 14 and the treatment tank circulation conduit 40 or the state of communicating the circulation nozzle 14 and the water supply conduit 43.

The water supply conduit 43 communicates the three-way valve 42 and a water supply source connection portion 46. The water supply conduit 43 is provided with a water introducing valve 45 that opens and closes the water supply conduit 43 and a water filter 44 that filters the water. The water supply source connection portion 46 is connected to a water supply source 49 such as a waterworks that sends out the water through a hose or the like for example.

In a section between the water filter 44 and the three-way valve 42 in the water supply conduit 43, a dilution valve 47 is provided. To the dilution valve 47, a dilution conduit 48 that communicates the dilution valve 47 and the medicinal solution storage portion 20 is connected. The dilution valve 47 can be switched to the state of communicating the water filter 44 and the three-way valve 42, or the state of communicating the water filter 44 and the dilution conduit 48.

In the case that the liquid is stored inside the treatment tank 2, when the three-way valve 42 is turned to the state of communicating the circulation nozzle 14 and the treatment tank circulation conduit 40, the dilution valve 47 is turned to the state of communicating the water filter 44 and the three-way valve 42, and the operation of the liquid flow pump 41 is started, the liquid inside the treatment tank 2 is discharged from the circulation nozzle 14 through the circulation port 13, the circulation conduit 13a, and the treatment tank circulation conduit 40.

In addition, when the three-way valve 42 is turned to the state of communicating the circulation nozzle 14 and the water supply conduit 43, the dilution valve 47 is turned to the state of communicating the water filter 44 and the three-way valve 42, and the water introducing valve 45 is turned to an open state, the water supplied from the water supply source 49 is discharged from the circulation nozzle 14. The liquid discharged from the circulation nozzle 14 is introduced into the treatment tank 2.

In addition, when the dilution valve 47 is turned to the state of communicating the water filter 44 and the dilution conduit 48 and the water introducing valve 45 is turned to the open state, the water supplied from the water supply source 49 is introduced into the medicinal solution storage portion 20.

The cleaning solution nozzle 15 is an opening portion communicated with a cleaning solution tank 50 that stores the cleaning solution through a cleaning solution conduit 51. The cleaning solution is used in the cleaning treatment. The cleaning solution conduit 51 is provided with a cleaning solution pump 52. By operating the cleaning solution pump 52, the cleaning solution inside the cleaning solution tank 50 is transferred into the treatment tank 2.

In addition, the endoscope reprocessor 1 includes an operation portion 7 and an output portion 8 configuring a user interface that gives and receives information to/from a user. The operation portion 7 and the output portion 8 are electrically connected to the control portion 5.

The operation portion 7 includes operation members such as a push switch and a touch sensor. In addition, the output portion 8 includes a display device that displays images and characters for example, a light emitting device that emits light, a speaker that emits sound, or the combination. Note that the operation portion 7 and the output portion 8 may be in a form of being provided in an electronic device that performs wireless communication with the control portion 5.

Figure 2:
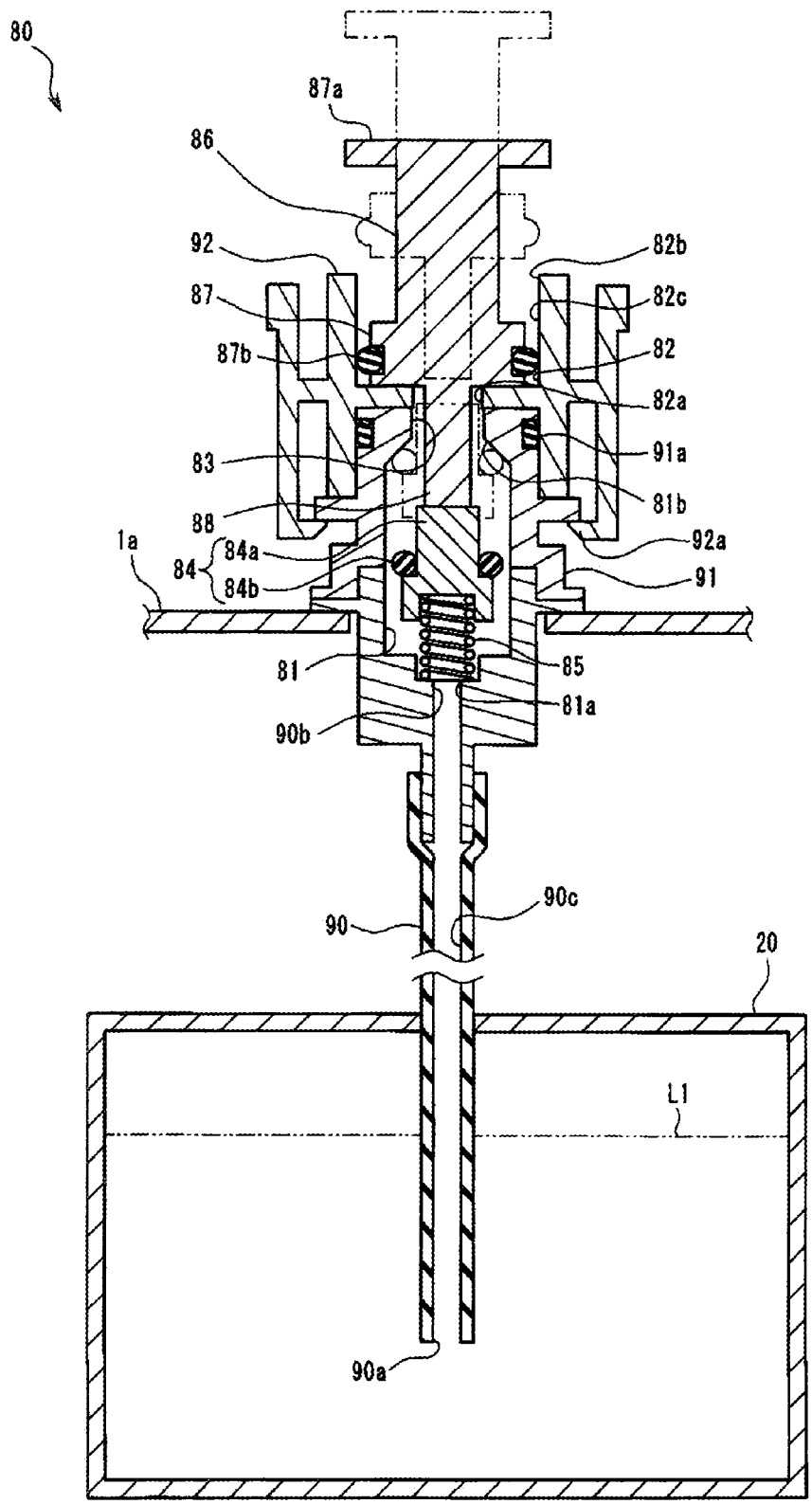
FIG. 2 is a sectional view illustrating a configuration of a medicinal solution storage portion and a medicinal solution sampling portion of the first embodiment.

As illustrated in FIG. 2, the medicinal solution sampling portion 80 includes the sampling tube 90, a first chamber 81, a second chamber 82, a constricted portion 83, a first advancing/retreating portion 84, and an energizing portion 85. In addition, the medicinal solution sampling portion 80 includes a plunger 86.

The sampling tube 90 includes a passage 90c that communicates an opening provided on the first end portion 90a and an opening provided on a second end portion 90b. The first end portion 90a of the sampling tube 90 is arranged at or below a predetermined water level L1 inside the medicinal solution storage portion 20, and the second end portion 90b is arranged at a position higher than the predetermined water level L1 outside the medicinal solution storage portion 20. That is, in the case that the medicinal solution is stored to the predetermined water level L1 inside the medicinal solution storage portion 20, the first end portion 90a of the sampling tube 90 sinks under the medicinal solution. It is preferable that the sampling tube 90 is configured by a highly water-repellent material or surface treatment of improving water repellency is executed to an inner peripheral surface of the passage 90c.

The opening provided on the first end portion 90a is opened to a space inside the medicinal solution storage portion 20. The opening on the second end portion 90b is connected to a space inside the first chamber 81 described later.

The first chamber 81 and the second chamber 82 are the space connected by the constricted portion 83. That is, the second chamber 82 is connected to the second end portion 90b of the sampling tube 90 through the constricted portion 83 and the first chamber 81. The second chamber 82 is communicated with the constricted portion 83 as described above and also opened to the outside through an opening portion 82b. In addition, the second chamber 82 is arranged at a position higher than the first chamber 81.

More specifically, the first chamber 81 is formed inside a base portion 91. In addition, the second chamber 82 is formed inside a cylinder portion 92 attachable and detachable to/from the base portion 91. Note that the cylinder portion 92 may be integrated with the base portion 91. It is preferable that the base portion 91 and the cylinder portion 92 are configured by the high water-repellent material or the surface treatment of improving the water repellency is executed to inner surfaces of the first chamber 81 and the second chamber 82.

The base portion 91 is fixed to a body portion 1a of the endoscope reprocessor 1. The first chamber 81 is arranged at a position higher than the predetermined water level L1 inside the medicinal solution storage portion 20. A part where the base portion 91 is fixed in the endoscope reprocessor 1 is not limited in particular as long as it is the part that causes the first chamber 81 to be arranged at the position higher than the predetermined water level L1 inside the medicinal solution storage portion 20. It is preferable that the base portion 91 can be visually recognized easily by the user of the endoscope reprocessor 1 and is arranged at a position that a hand can reach.

In the present embodiment, as one example, the base portion 91 is fixed to an upper surface of the body portion 1a of the endoscope reprocessor 1. Note that the base portion 91 may be fixed inside the treatment tank 2 for example. In addition, for example, the base portion 91 may be fixed to an inner side of an openable/closable door provided on the body portion 1a for example.

The first chamber 81 is provided with two openings, a lower side opening 81a which is one opening is communicated with the opening on the second end portion 90b of the sampling tube 90, and an upper side opening 81b which is the other opening is communicated with the constricted portion 83 described later. The upper side opening 81b is provided on a position higher than the lower side opening 81a.

In the present embodiment, as one example, the first chamber 81 is a columnar space, a center axis of which extends in a vertical direction. Note that a sectional shape of the first chamber 81 is not limited to a circular shape and may be a polygonal shape, an elliptic shape or the like. The lower side opening 81a is formed on a lower surface of the first chamber 81. In addition, the upper side opening 81b is formed on an upper surface of the first chamber 81. The upper side opening 81b has an inner diameter smaller than an inner diameter of the first chamber 81. The upper side opening 81b is formed on the center axis of the first chamber 81.

The constricted portion 83 is a through-hole that communicates an outer side of the base portion 91 and the first chamber 81. The constricted portion 83 is opened to the outer side of the base portion 91 at an upper end of the base portion 91. The constricted portion 83 has an inner diameter smaller than the inner diameter of the first chamber 81. In the present embodiment, as one example, the constricted portion 83 is formed on the center axis of the first chamber 81 at the upper end of the base portion 91.

The second chamber 82 is a space formed inside the cylinder portion 92 attachable and detachable to/from the base portion 91. The second chamber 82 is provided with two openings, and a communication port 82a which is one opening is communicated with the constricted portion 83 in the state that the cylinder portion 92 is fixed to the base portion 91. That is, the second chamber 82 is attachable and detachable to/from the constricted portion 83.

In addition, the opening portion 82b which is the other opening of the second chamber 82 is opened to the outside of the cylinder portion 92. In the state that the cylinder portion 92 is fixed to the base portion 91, the opening portion 82b is provided on a position higher than the communication port 82a.

In the present embodiment, as one example, the cylinder portion 92 is in a cylindrical shape, and is fixed to the base portion 91 by engagement with the base portion 91 of a claw-like engaging portion 92a provided on an outer peripheral portion. Note that a configuration for fixing the cylinder portion 92 to the base portion 91 is not limited to the present embodiment and may be a screw mechanism for example.

A center axis of the cylinder portion 92 in the cylindrical shape extends in the vertical direction in the state of being fixed to the base portion 91. Then, the second chamber 82 is a columnar space of a constant diameter, which is formed inside the cylinder portion 92. The communication port 82a is the opening formed at a lower end of the second chamber 82. In addition, the opening portion 82b has an inner diameter equal to or larger than the inner diameter of the second chamber 82.

That is, in the state that the cylinder portion 92 is fixed to the base portion 91, the second chamber 82 is the inside of a recessed portion where the opening portion 82b is opened upwards, and the communication port 82a is opened on a bottom surface of the second chamber 82.

In addition, in the state that the cylinder portion 92 is fixed to the base portion 91, a center axis of the communication port 82a roughly coincides with the center axis of the first chamber 81, and the communication port 82a is communicated with the constricted portion 83 opened at the upper end of the base portion 91.

That is, in the state that the cylinder portion 92 is fixed to the base portion 91, the second chamber 82 is arranged above the first chamber 81, and the constricted portion 83 connects the upper side opening 81b of the first chamber 81 and the communication port 82a of the second chamber 82. Between the base portion 91 and the cylinder portion 92, a sealing member 91a configured to prevent leakage of the gas from a connection portion of the communication port 82a and the constricted portion 83 is provided.

The first advancing/retreating portion 84 is arranged inside the first chamber 81. The first advancing/retreating portion 84 advances and retreats between a first position to close the upper side opening 81b or the constricted portion 83 and a second position to open the upper side opening 81b or the constricted portion 83.

More specifically, the first advancing/retreating portion 84 advances and retreats in the vertical direction inside the first chamber 81. An upper end of a moving range of the first advancing/retreating portion 84 is the first position. The first advancing/retreating portion 84 blocks the upper side opening 81b or the constricted portion 83 in the state being positioned at the first position.

The configuration of blocking the upper side opening 81b or the constricted portion 83 by the first advancing/retreating portion 84 is not limited in particular. For example, the first advancing/retreating portion 84 may be a lid-like member that closes the upper side opening 81b by being in close contact with a periphery of the upper side opening 81b on the upper surface of the first chamber 81, in the state of being positioned at the first position. In addition, for example, the first advancing/retreating portion 84 may be a plug-like member that closes the constricted portion 83 by being inserted into the constricted portion 83 and being in close contact with an inner peripheral surface of the constricted portion 83, in the state of being positioned at the first position.

The first advancing/retreating portion 84 opens the upper side opening 81b or the constricted portion 83 at a point of time of reaching the second position by moving downwards from the upper end (first position) of the moving range. Here, the second position does not indicate one specific point in the moving range of the first advancing/retreating portion 84, but the second position is a range of a predetermined width in which the upper side opening 81b or the constricted portion 83 becomes the open state in the moving range of the first advancing/retreating portion 84. In the case that the first advancing/retreating portion 84 is positioned at the second position, traffic of the fluid through the constricted portion 83 becomes possible between the first chamber 81 and the second chamber 82.

Figure 3:
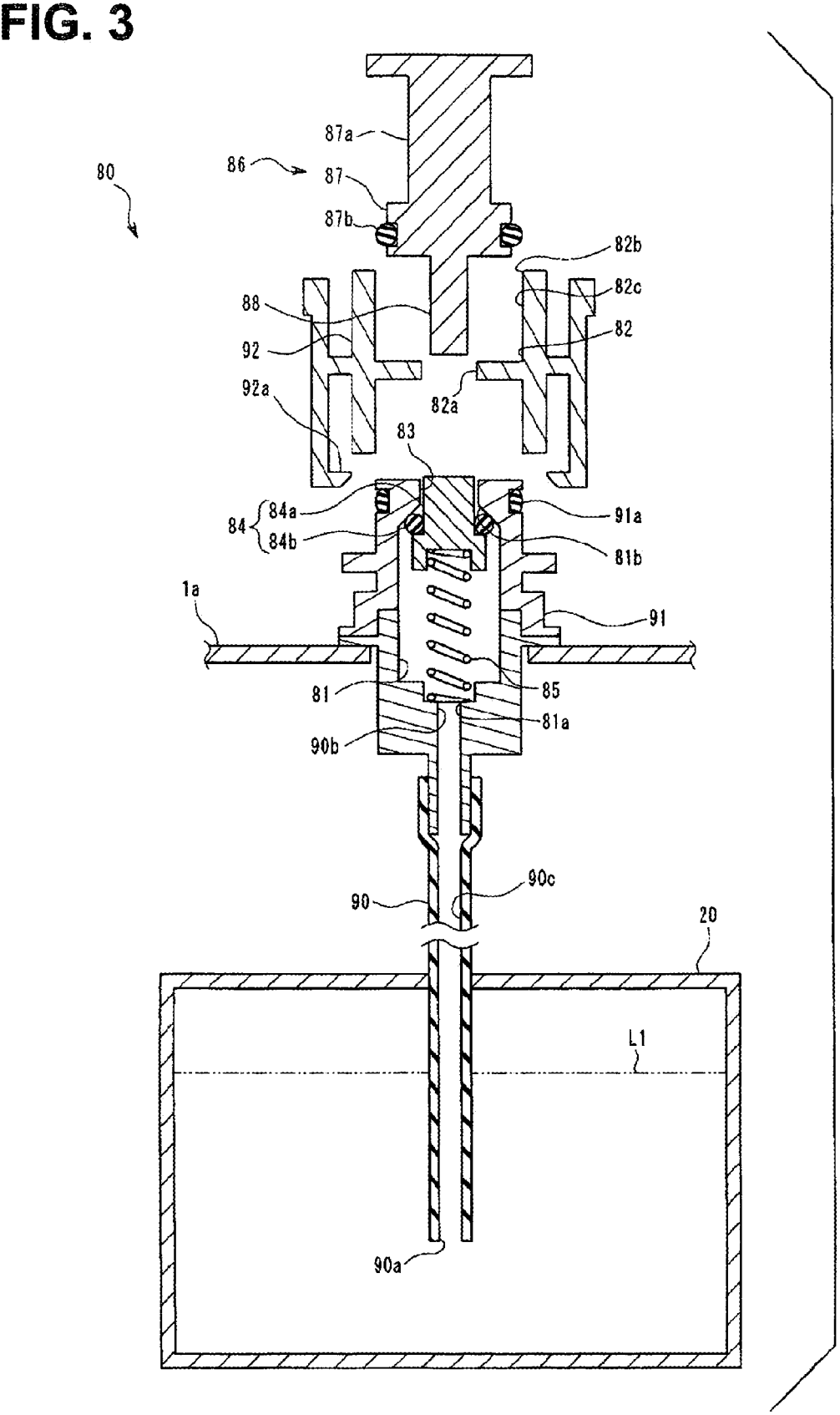
FIG. 3 is a sectional view illustrating a state that a second chamber and a plunger are detached from the first chamber, in the first embodiment.

The first advancing/retreating portion 84 is energized in a direction from the second position to the first position by the energizing portion 85. That is, as illustrated in FIG. 3, the first advancing/retreating portion 84 is positioned at the first position in the case that force from somewhere other than the energizing portion 85 is not applied. The energizing portion 85 may be configured to generate energizing force by a metallic or resin-made spring, or may be configured to generate the energizing force by magnetic force. In the case that the energizing portion 85 is configured to generate the energizing force by the magnetic force, one of the first advancing/retreating portion 84 and the constricted portion 83 includes a magnet and the other includes a magnetic body such as iron to be attracted to the magnet, for example.

In the present embodiment, as one example, the first advancing/retreating portion 84 includes a columnar advancing portion 84a that advances into the constricted portion 83 at the first position, and an annular retention portion 84b arranged on an outer periphery of the advancing portion 84a.

The advancing portion 84a is a columnar part smaller than the inner diameter of the constricted portion 83, and reduces an opening area of the constricted portion 83 by advancing into the constricted portion 83. The retention portion 84b is an elastic portion formed of an elastic material such as rubber, and comes into close contact with the periphery of the upper side opening 81b on the upper surface of the first chamber 81 in the state that the first advancing/retreating portion 84 is positioned at the first position. Therefore, in the state that the first advancing/retreating portion 84 is positioned at the first position, the upper side opening 81b is blocked by the advancing portion 84a and the retention portion 84b. Note that, when the first advancing/retreating portion 84 is configured by the elastic material such as rubber, the advancing portion 84a and the retention portion 84b can be integrally configured.

In the case of moving the first advancing/retreating portion 84 from the second position to the first position, the advancing portion 84a advances into the constricted portion 83 at the point of time before the first advancing/retreating portion 84 reaches the first position. That is, in the case that the first advancing/retreating portion 84 moves from the second position to the first position, the opening area of the constricted portion 83 is narrowed by the advancing portion 84a before the upper side opening 81b is blocked.

In addition, in the present embodiment, as one example, the energizing portion 85 is a compression coil spring held between the first advancing/retreating portion 84 and the lower surface of the first chamber 81 inside the first chamber 81. By the energizing force of the energizing portion 85, the first advancing/retreating portion 84 is energized upwards. A position at which the retention portion 84b comes into contact with the upper surface of the first chamber 81 by the energizing force of the energizing portion 85 is the first position which is the upper end of the moving range of the first advancing/retreating portion 84. In other words, the retention portion 84b retains the first chamber portion 81 including the advancing portion 84a by coming into contact with the upper surface of the first chamber 81.

Note that, in the present embodiment, the first advancing/retreating portion 84 opens and closes the upper side opening 81b or the constricted portion 83 by advancing and retreating along the center axis of the first chamber 81 inside the first chamber 81, however, the configuration of the first advancing/retreating portion 84 is not limited to the present embodiment. For example, the first advancing/retreating portion 84 may be configured to swing around a rotary axis provided inside the first chamber 81 to open and close the upper side opening 81b or the constricted portion 83.

The plunger 86 includes a second advancing/retreating portion 87 and a holding portion 88. Note that, while the second advancing/retreating portion 87 and the holding portion 88 are integrated in the present embodiment, both may be separable.

The second advancing/retreating portion 87 is a columnar member that can be inserted from the outside of the second chamber 82 into the second chamber 82 through the opening portion 82b. The second advancing/retreating portion 87 can advance and retreat in the vertical direction inside the second chamber 82. The second advancing/retreating portion 87 is provided with a handle portion 87a exposed in an upper direction from the opening portion 82b in the state that the second advancing/retreating portion 87 is inserted into the second chamber 82.

In addition, on the outer periphery of the second advancing/retreating portion 87, a slidable contact portion 87b to be in airtight contact with an inner peripheral surface 82c of the second chamber 82 in the state that the second advancing/retreating portion 87 is inserted into the second chamber 82 is provided. In the state that the second advancing/retreating portion 87 is inserted into the second chamber 82, an area below the slidable contact portion 87b in the second chamber 82 is sealed by the second advancing/retreating portion 87 and the slidable contact portion 87b.

That is, the second advancing/retreating portion 87 is a piston-like member to be inserted into the cylinder-like second chamber 82. By the second advancing/retreating portion 87 advancing and retreating inside the second chamber 82, a volume of the second chamber 82 is changed. Note that, when the second advancing/retreating portion 87 is configured by the elastic material such as rubber, the second advancing/retreating portion 87 and the slidable contact portion 87b can be integrally configured.

In the present embodiment, as one example, the second advancing/retreating portion 87 has a columnar shape to be fitted with a predetermined gap inside the second chamber 82. On an outer peripheral surface of the second advancing/retreating portion 87, the annular slidable contact portion 87b that fills the gap with the inner peripheral surface 82c of the second chamber 82 is provided.

The holding portion 88 is connected to the second advancing/retreating portion 87, and is projected toward the inside of the communication port 82a of the second chamber 82 in the state that the second advancing/retreating portion 87 is inserted into the second chamber 82. The holding portion 88 advances and retreats inside the second chamber 82 together with the second advancing/retreating portion 87.

In the case that the slidable contact portion 87b of the second advancing/retreating portion 87 is in airtight contact with the inner peripheral surface 82c of the second chamber 82, the holding portion 88 extends into the constricted portion 83 or into the first chamber 81 and comes into contact with the first advancing/retreating portion 84. Then, in the case that the slidable contact portion 87b of the second advancing/retreating portion 87 is in airtight contact with the inner peripheral surface 82c of the second chamber 82, the holding portion 88 moves the first advancing/retreating portion 84 to the second position opposing the energizing force of the energizing portion 85.

Figure 4:
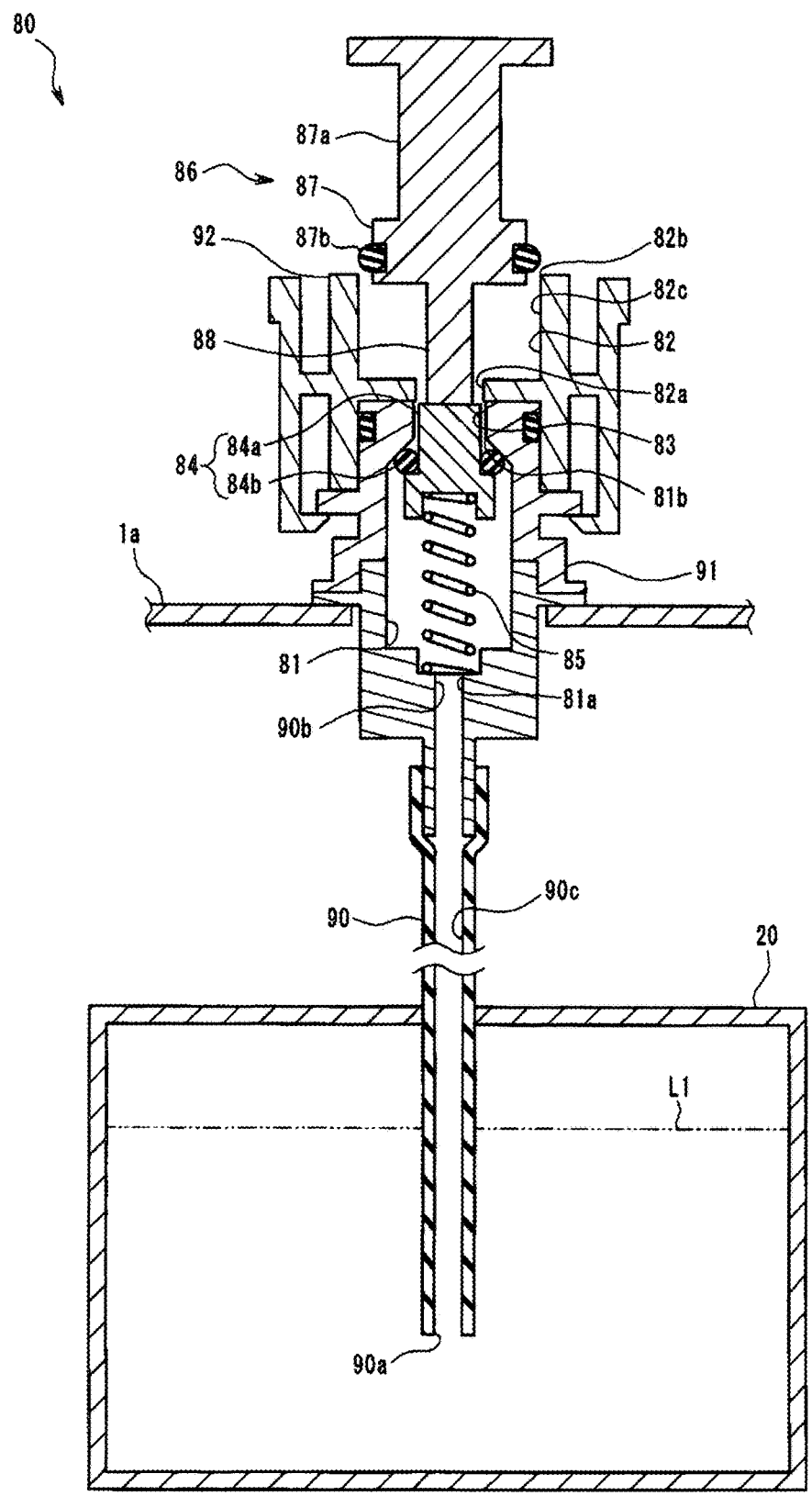
FIG. 4 is a diagram illustrating a position of a second advancing/retreating portion in a case that a first advancing/retreating portion is positioned at a first position, in the first embodiment.

As illustrated in FIG. 4, in the case that the first advancing/retreating portion 84 is positioned at the first position, the slidable contact portion 87b of the second advancing/retreating portion 87 is out of the inside of the second chamber 82, and the second chamber 82 is opened to the outside.

In the present embodiment, as one example, the holding portion 88 is a columnar part projected from a lower end of the second advancing/retreating portion 87 along the center axis of the second advancing/retreating portion 87 in the columnar shape. The holding portion 88 is narrower than the inner diameter of the communication port 82a and the constricted portion 83.

In the case of inserting the second advancing/retreating portion 87 from the opening portion 82b into the second chamber 82, the holding portion 88 advances into the communication port 82a and the constricted portion 83, and the holding portion 88 comes into contact with the advancing portion 84a of the first advancing/retreating portion 84 before the slidable contact portion 87b comes into close contact with the inner peripheral surface 82c of the second chamber 82.

In addition, in the present embodiment, in the case that the slidable contact portion 87b of the second advancing/retreating portion 87 is in contact with the upper end of the inner peripheral surface 82c of the second chamber 82, the advancing portion 84a of the first advancing/retreating portion 84 is inside the constricted portion 83. In other words, when the first advancing/retreating portion 84 held by the holding portion 88 is at the second position and the slidable contact portion 87b of the second advancing/retreating portion 87 is in close contact with the inner peripheral surface 82c of the second chamber 82, the advancing portion 84a is inside the constricted portion 83.

Next, an operation of sampling the medicinal solution by the medicinal solution sampling portion 80 including the configuration described above will be described.

Figure 5:
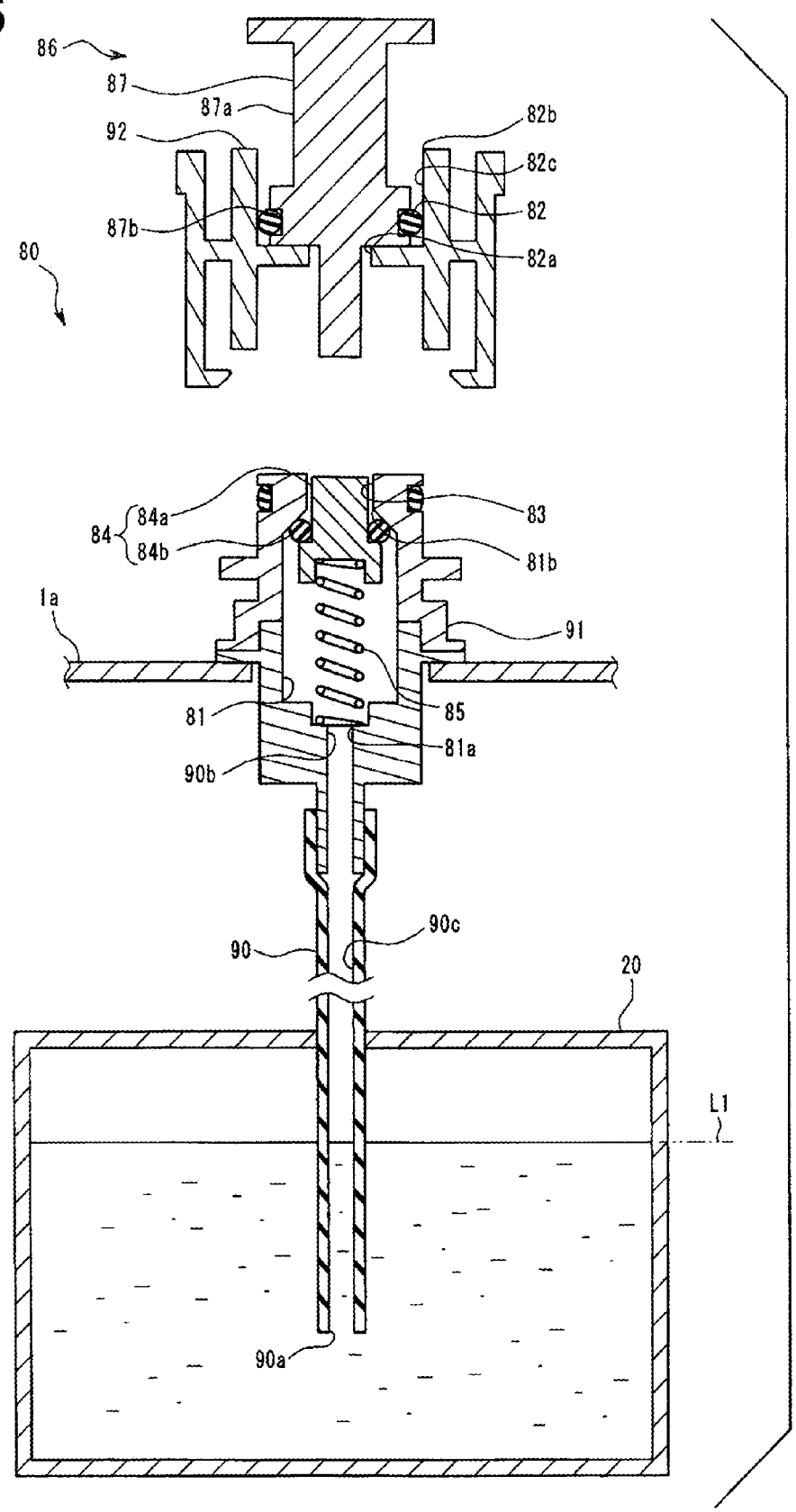
FIG. 5 is a diagram illustrating an operation when sampling a medicinal solution, in the first embodiment.

The medicinal solution can be sampled by the medicinal solution sampling portion 80 in the case that the medicinal solution is stored inside the medicinal solution storage portion 20 up to the predetermined water level L1. In the following description, as illustrated in FIG. 5, it is assumed that the medicinal solution is stored up to the predetermined water level L1 inside the medicinal solution storage portion 20. That is, in the state that the first end portion 90a of the sampling tube 90 sinks under the medicinal solution inside the medicinal solution storage portion 20, sampling of the medicinal solution by the medicinal solution sampling portion 80 described below is performed.

FIG. 5 illustrates the state before starting the operation of sampling the medicinal solution. In the case of executing the reprocessing treatment by the endoscope reprocessor 1, the medicinal solution sampling portion 80 is turned to the state illustrated in FIG. 5. As illustrated in FIG. 5, in the case of not using the medicinal solution sampling portion 80, the plunger 86 and the cylinder portion 92 are turned to the state of being detached from the second chamber 82. In this case, the first advancing/retreating portion 84 is positioned at the first position by the energizing force of the energizing portion 85 and the upper side opening 81b of the first chamber 81 is blocked by the first advancing/retreating portion 84.

Figure 6:
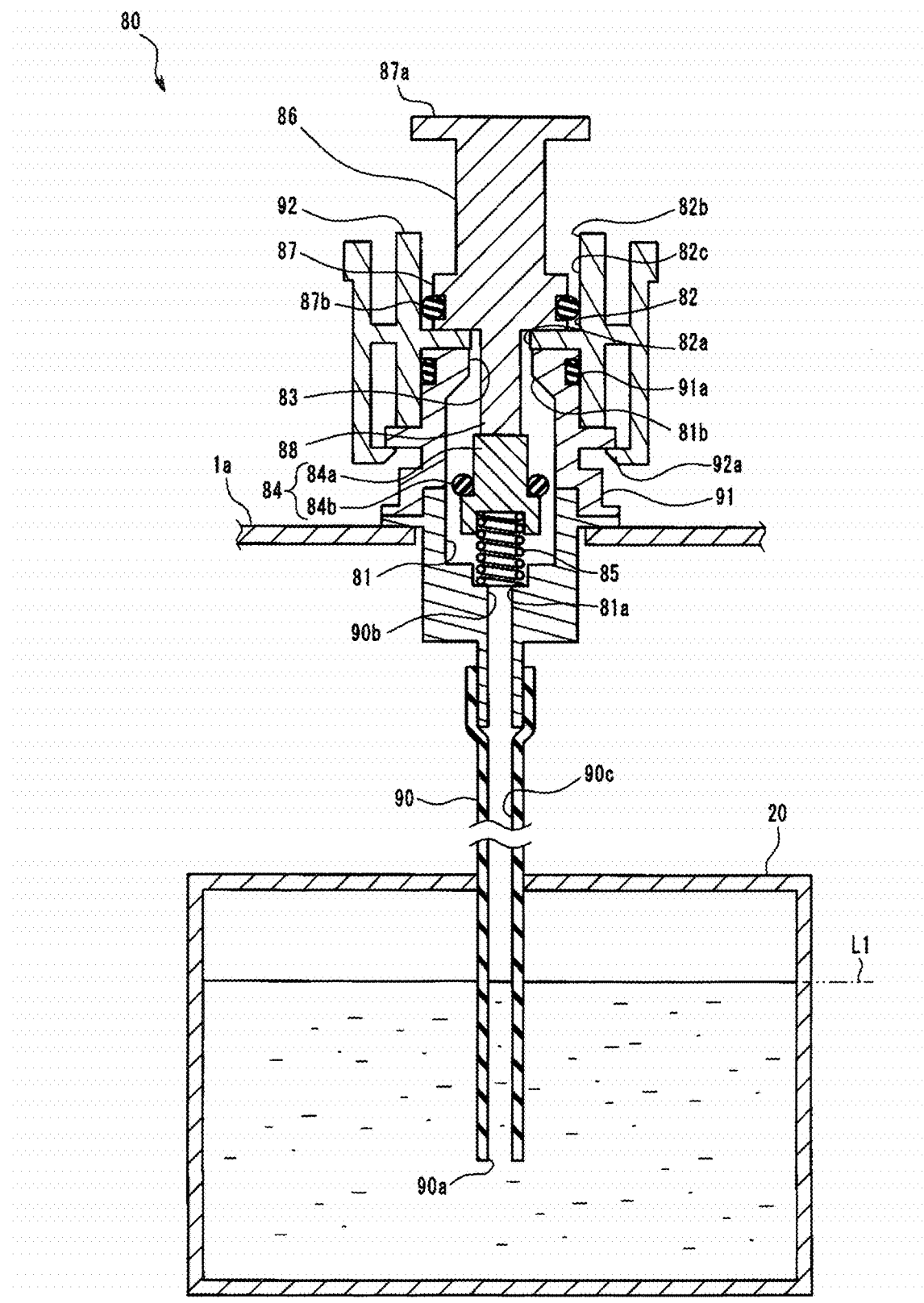
FIG. 6 is a diagram illustrating an operation when sampling the medicinal solution, in the first embodiment.

In the case of using the medicinal solution sampling portion 80, as illustrated in FIG. 6, the cylinder portion 92 is fixed to the base portion 91, and the second advancing/retreating portion 87 of the plunger 86 is inserted to a bottom inside the second chamber 82. By the operation, the first advancing/retreating portion 84 is pressurized by the holding portion 88 of the plunger 86, moved to a lower part of the first chamber 81 and positioned at the second position. By the first advancing/retreating portion 84 being positioned at the second position, the upper side opening 81b of the first chamber 81 is turned to the open state. In addition, since the second advancing/retreating portion 87 is inserted to the bottom inside the second chamber 82, the volume of the second chamber 82 is reduced.

Figure 7:
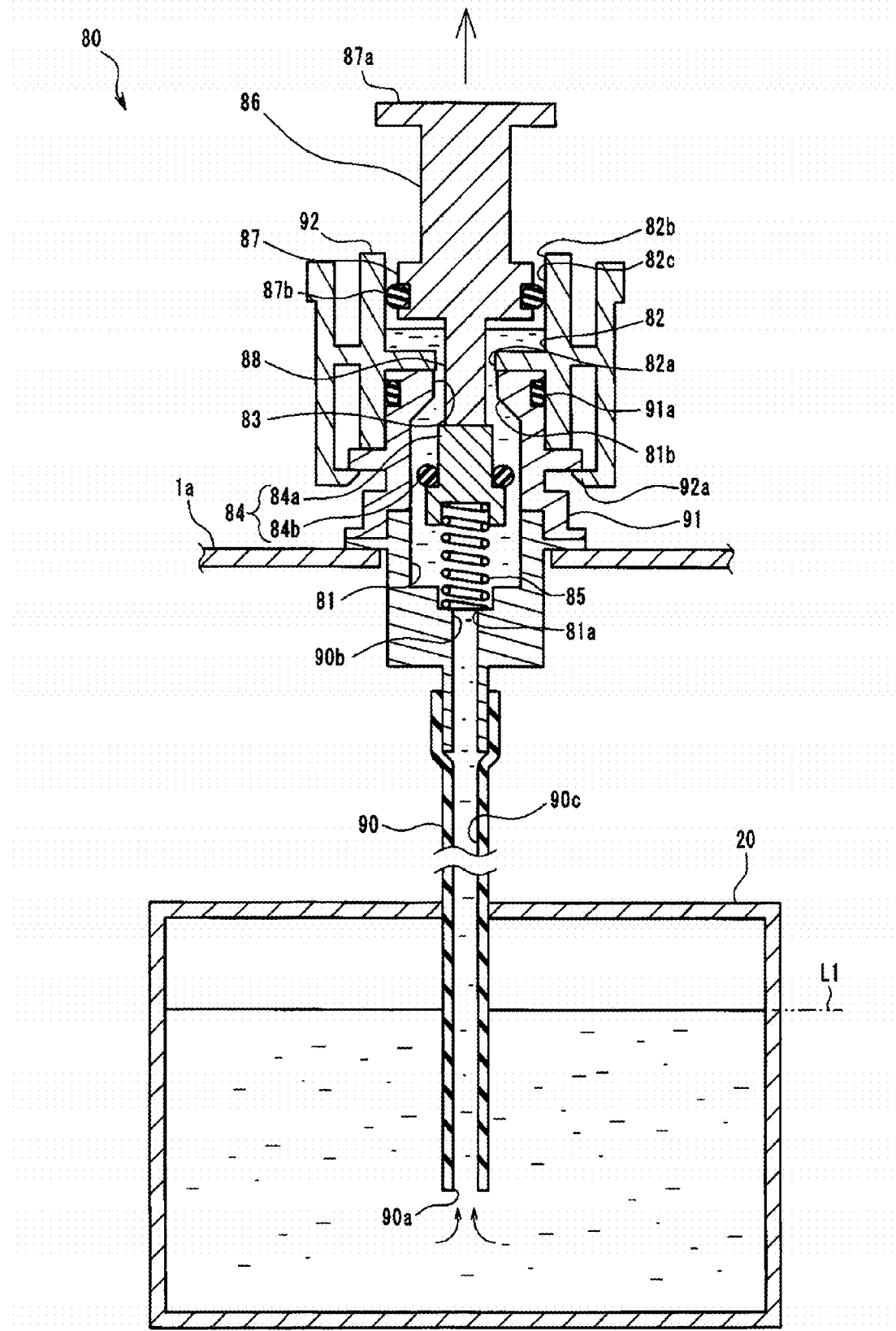
FIG. 7 is a diagram illustrating an operation when sampling the medicinal solution, in the first embodiment.
Figure 8:
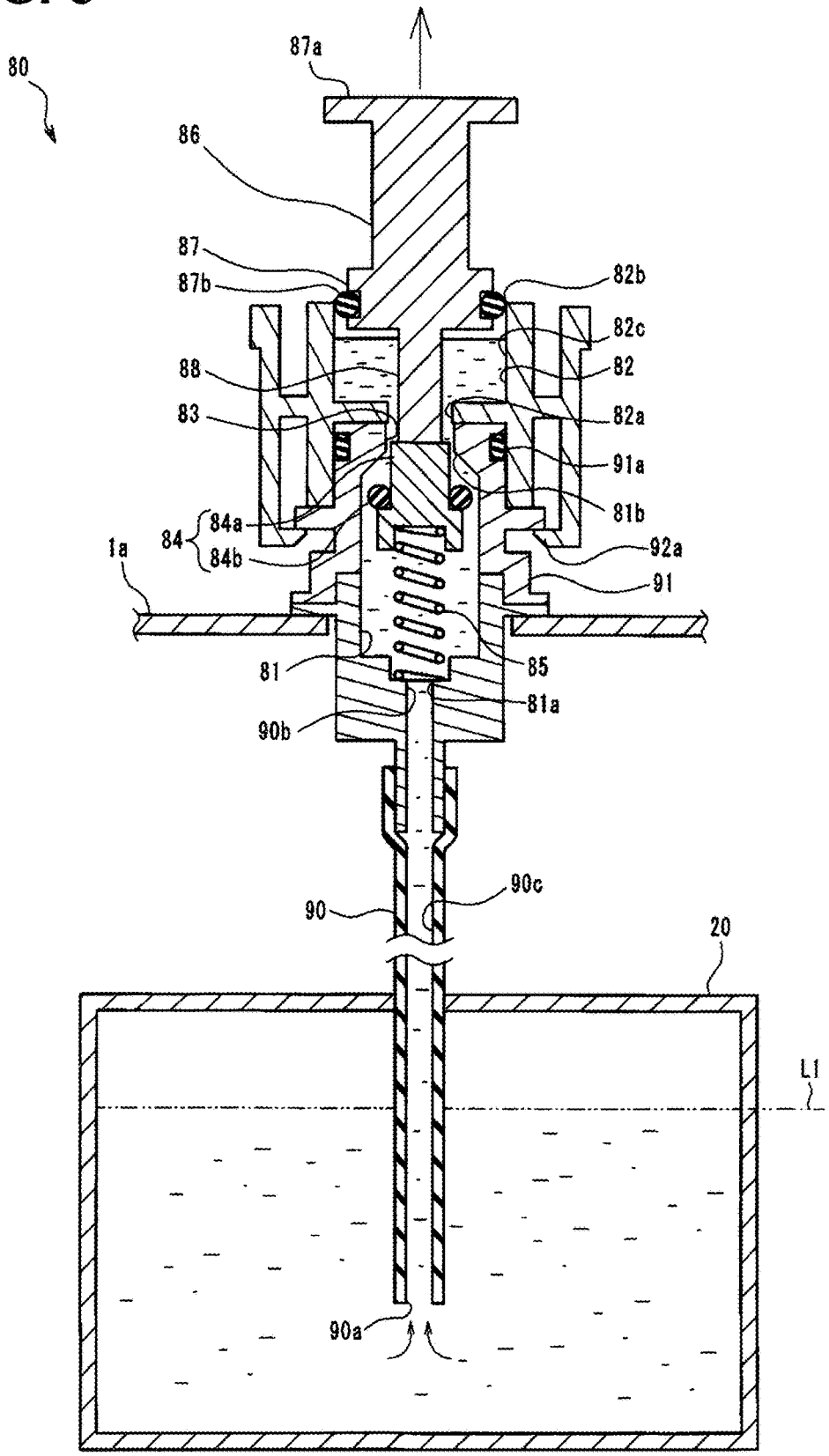
FIG. 8 is a diagram illustrating an operation when sampling the medicinal solution, in the first embodiment.
Figure 9:
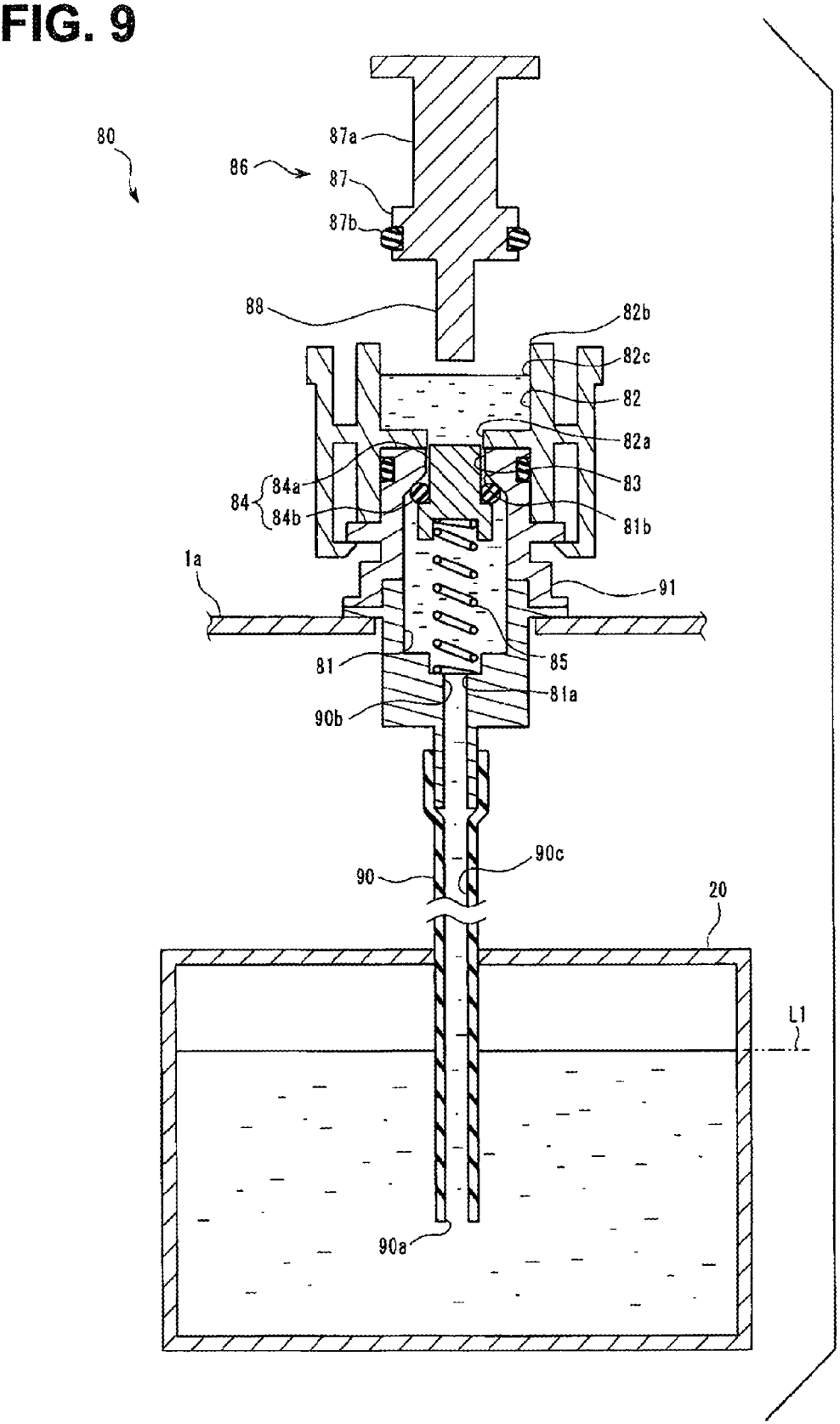
FIG. 9 is a diagram illustrating an operation when sampling the medicinal solution, in the first embodiment.

Next, as illustrated in FIG. 7 to FIG. 9, the plunger 86 is pulled upwards, and the second advancing/retreating portion 87 is pulled out from the inside of the second chamber 82. Stages illustrated in FIG. 7 to FIG. 9 are continuously shifted without stopping.

By pulling the plunger 86 upwards, the second advancing/retreating portion 87 is elevated inside the second chamber 82. Since the second advancing/retreating portion 87 is moved while being in airtight contact with the inner peripheral surface 82c of the second chamber 82 at the slidable contact portion 87b, an air pressure inside the second chamber 82 declines as the second advancing/retreating portion 87 is elevated.

In addition, at the time, the first advancing/retreating portion 84 is in contact with the holding portion 88 of the plunger 86 and is positioned at the second position, and the upper side opening 81b of the first chamber 81 is turned to the open state. That is, the second chamber 82 is in the state of being communicated with the first chamber 81 through the communication port 82a, the constricted portion 83 and the upper side opening 81b.

Therefore, inside the second chamber 82, by pulling up the second advancing/retreating portion 87 from the lower end, the air pressure inside the second chamber 82, the first chamber 81 and the passage 90c of the sampling tube 90 communicated with the first chamber 81 declines, and as illustrated in FIG. 7, the medicinal solution inside the medicinal solution storage portion 20 is sucked up to the inside of the second chamber 82 through the sampling tube 90 and the first chamber 81.

In the stage that the plunger 86 is pulled up and the slidable contact portion 87b of the second advancing/retreating portion 87 reaches the upper end of the inner peripheral surface 82c of the second chamber 82, as illustrated in FIG. 8, the first advancing/retreating portion 84 is positioned at the second position by pressurization of the holding portion 88, and the second chamber 82 is kept in the state of being communicated with the first chamber 81. Therefore, the second advancing/retreating portion 87 can be easily pulled out from the inside of the second chamber 82. For example, when the upper side opening 81b is blocked by the first advancing/retreating portion 84 before the second advancing/retreating portion 87 is pulled out from the inside of the second chamber 82, force needed to pull out the second advancing/retreating portion 87 from the sealed second chamber 82 becomes large.

Then, as illustrated in FIG. 9, in the stage that the second advancing/retreating portion 87 is out of the inside of the second chamber 82, since the holding portion 88 of the plunger 86 is separated from the first advancing/retreating portion 84, the first advancing/retreating portion 84 is positioned at the first position and blocks the upper side opening 81b. Therefore, the medicinal solution sucked up to the inside of the second chamber 82 is kept stored inside the second chamber 82.

Note that, in the case of pulling out the second advancing/retreating portion 87 from the inside of the second chamber 82, since timing at which the slidable contact portion 87b of the second advancing/retreating portion 87 is separated from the inner peripheral surface 82c of the second chamber 82 is earlier than timing at which the upper side opening 81b is blocked by the first advancing/retreating portion 84, the air pressure inside the second chamber 82 returns to an atmospheric pressure, and a part of the medicinal solution drops into the medicinal solution storage portion 20.

However, in the present embodiment, in the case of pulling out the second advancing/retreating portion 87 from the inside of the second chamber 82, the advancing portion 84a of the first advancing/retreating portion 84 advances into the constricted portion 83 and the opening area of the constricted portion 83 is narrowed before the timing at which the slidable contact portion 87b of the second advancing/retreating portion 87 is separated from the inner peripheral surface 82c of the second chamber 82 and the air pressure inside the second chamber 82 becomes the atmospheric pressure. Therefore, an amount of the medicinal solution that drops into the medicinal solution storage portion 20 from the inside of the second chamber 82 is suppressed to a small amount.

Since the second chamber 82 after the second advancing/retreating portion 87 is pulled out is opened to the outside at the opening portion 82b, a medicinal effect confirmation test to the medicinal solution stored inside the second chamber 82 can be easily executed. The medicinal effect confirmation test is executed by immersing test paper for measuring a concentration of the medicinal solution for example in the medicinal solution stored in the second chamber 82. Note that the medicinal effect confirmation test may be executed by transferring the medicinal solution stored in the second chamber 82 to a testing device by a spuit or the like, for example.

Figure 10:
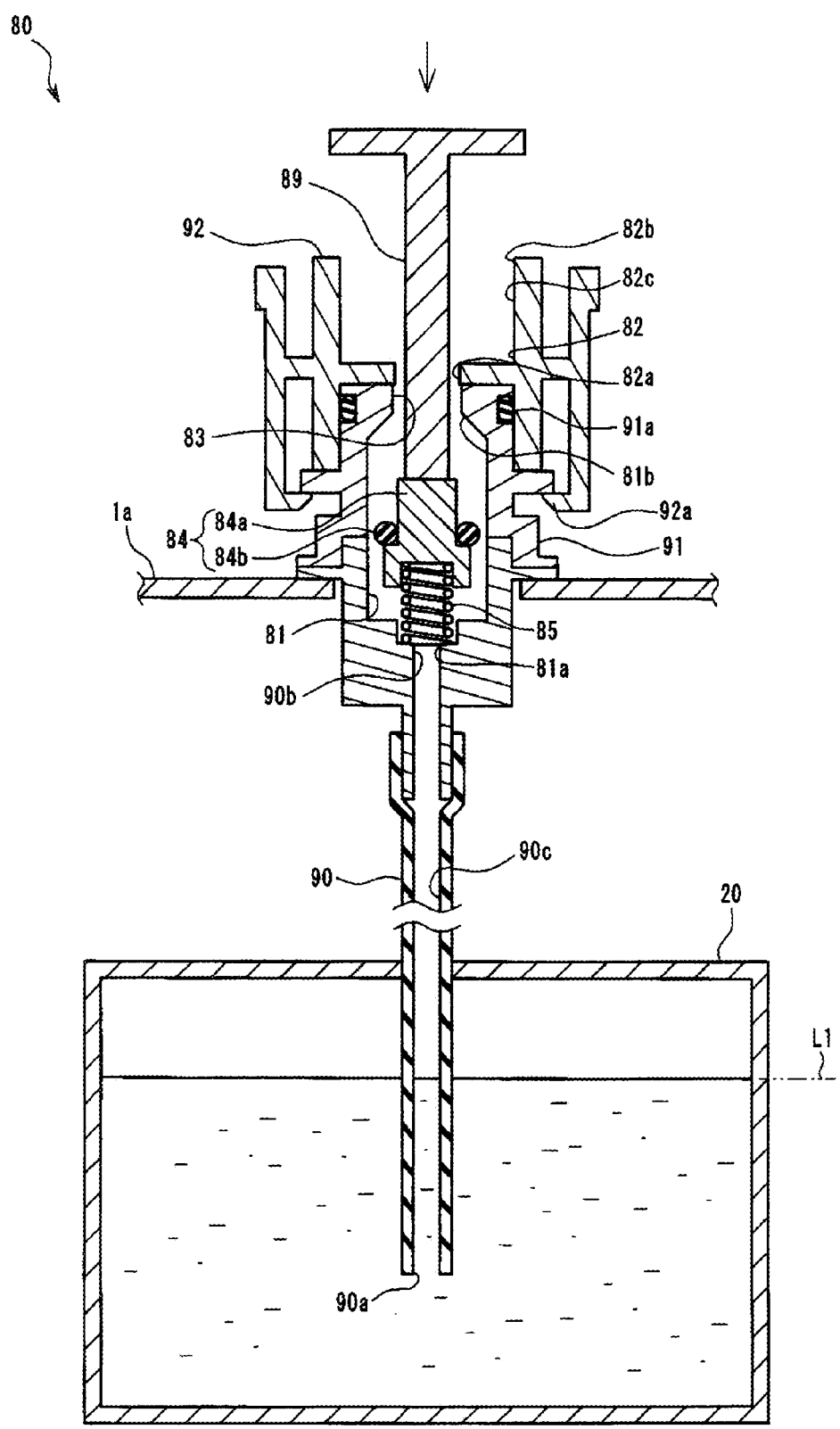
FIG. 10 is a diagram illustrating an operation when returning the medicinal solution, in the first embodiment.

Then, in the present embodiment, as illustrated in FIG. 10, by inserting a rod-like plug opener 89 for example to the communication port of the second chamber 82, pressurizing the first advancing/retreating portion 84 downwards and positioning the first advancing/retreating portion 84 at the second position, the medicinal solution stored inside the second chamber 82 can be returned to the inside of the medicinal solution storage portion 20 through the first chamber 81 and the sampling tube 90.

Note that the plug opener 89 may be the holding portion 88 of the plunger 86. In this case, by holding the plunger 86 at such a position that the first advancing/retreating portion 84 is held at the second position by the holding portion 88 but the second advancing/retreating portion 87 does not block the opening portion 82b of the second chamber 82, the medicinal solution stored inside the second chamber 82 can be returned to the inside of the medicinal solution storage portion 20.

Note that the plug opener 89 may be the plunger 86 itself used for sucking up the medicinal solution. In this case, the medicinal solution stored inside the second chamber 82 can be returned to the medicinal solution storage portion 20 regardless of a height positional relation between the medicinal solution storage portion 20 and the first chamber 81.

As described above, the endoscope reprocessor 1 of the present embodiment can suck up and store the medicinal solution stored inside the medicinal solution storage portion 20 inside the second chamber 82 by performing the operation of inserting the plunger 86 to the inside of the opening portion 82b of the second chamber 82 and then pulling out the plunger 86. In addition, in the present embodiment, by performing the operation of pressing down the first advancing/retreating portion 84 by the plug opener 89, the medicinal solution stored inside the second chamber 82 can be returned to the inside of the medicinal solution storage portion 20. In this way, according to the endoscope reprocessor 1 of the present embodiment, sampling of the medicinal solution from the medicinal solution storage portion 20 and return of the sampled medicinal solution to the medicinal solution storage portion 20 can be easily executed.

Modification of First Embodiment

Figure 11:
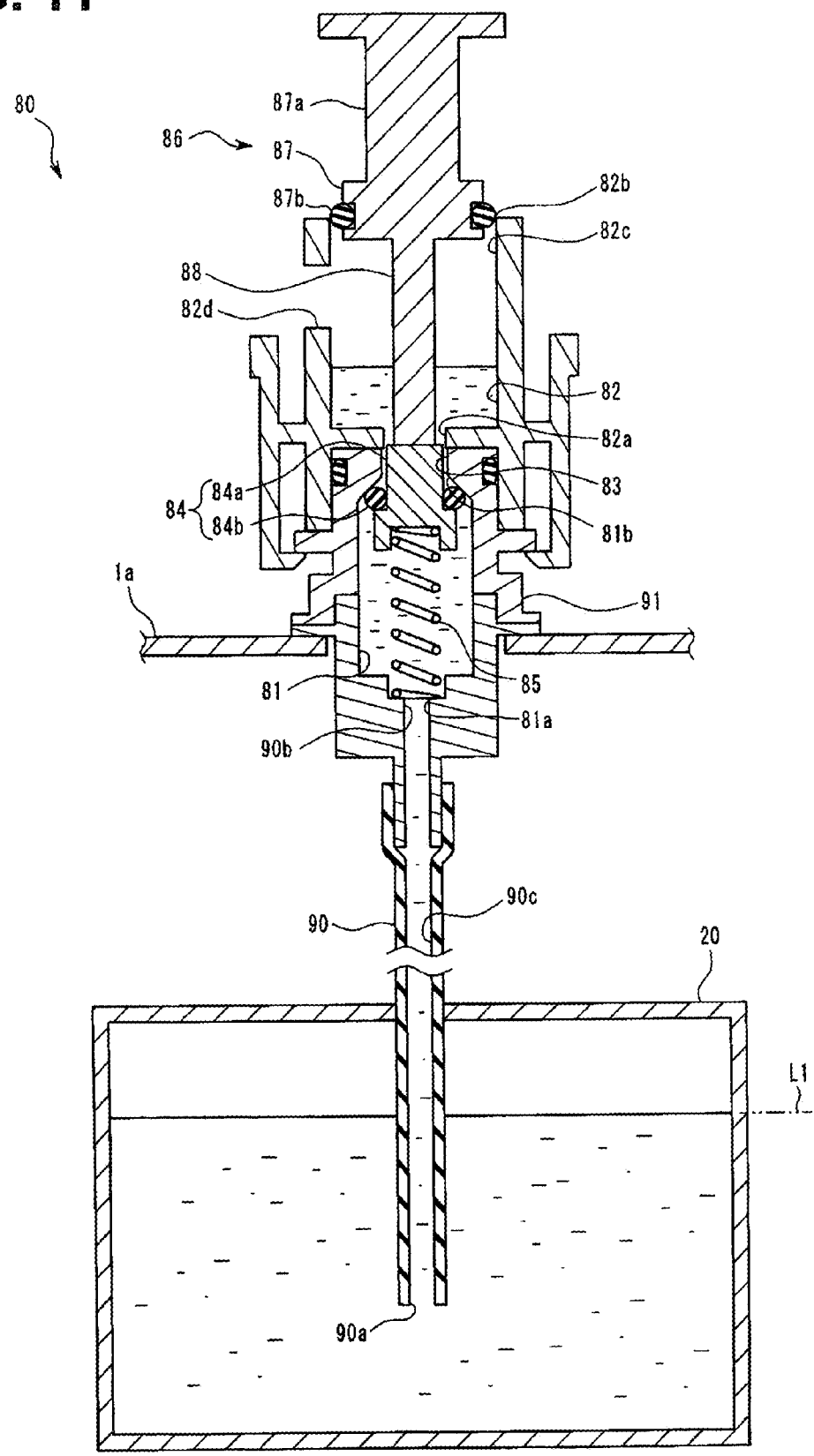
FIG. 11 is a diagram illustrating a modification of the first embodiment.

In the first embodiment of the present invention, an opening may be provided on a side face 82c of a second chamber side face portion as illustrated in FIG. 11 and may be turned to an inspection port 82d. By providing the inspection port 82d, the medicinal effect can be inspected from a side face opening portion without pulling out a second advancing/retreating portion. For example, the medicinal solution can be sampled by inserting a sampling tool such as a syringe to the inspection port 82d or the test paper can be inserted from the inspection port 82d.

Note that the timing at which the slidable contact portion 87b of the second advancing/retreating portion 87 reaches the side face opening portion in this case is earlier than the timing at which the upper side opening 81b is blocked by the first advancing/retreating portion 84.

In other words, differently from the first embodiment, in the modification, when the retention portion 84b is positioned at the constricted portion 83, the slidable contact portion 87b stays inside the side face 82c of the second chamber 82, and the inspection port 82d is positioned more on the side of the constricted portion 83 than the slidable contact portion 87 on the side face 82c.

Second Embodiment

Next, the second embodiment of the present invention will be described. Only differences from the first embodiment will be described below, same signs will be attached to components similar to those of the first embodiment, and the description will be appropriately omitted.

Figure 12:
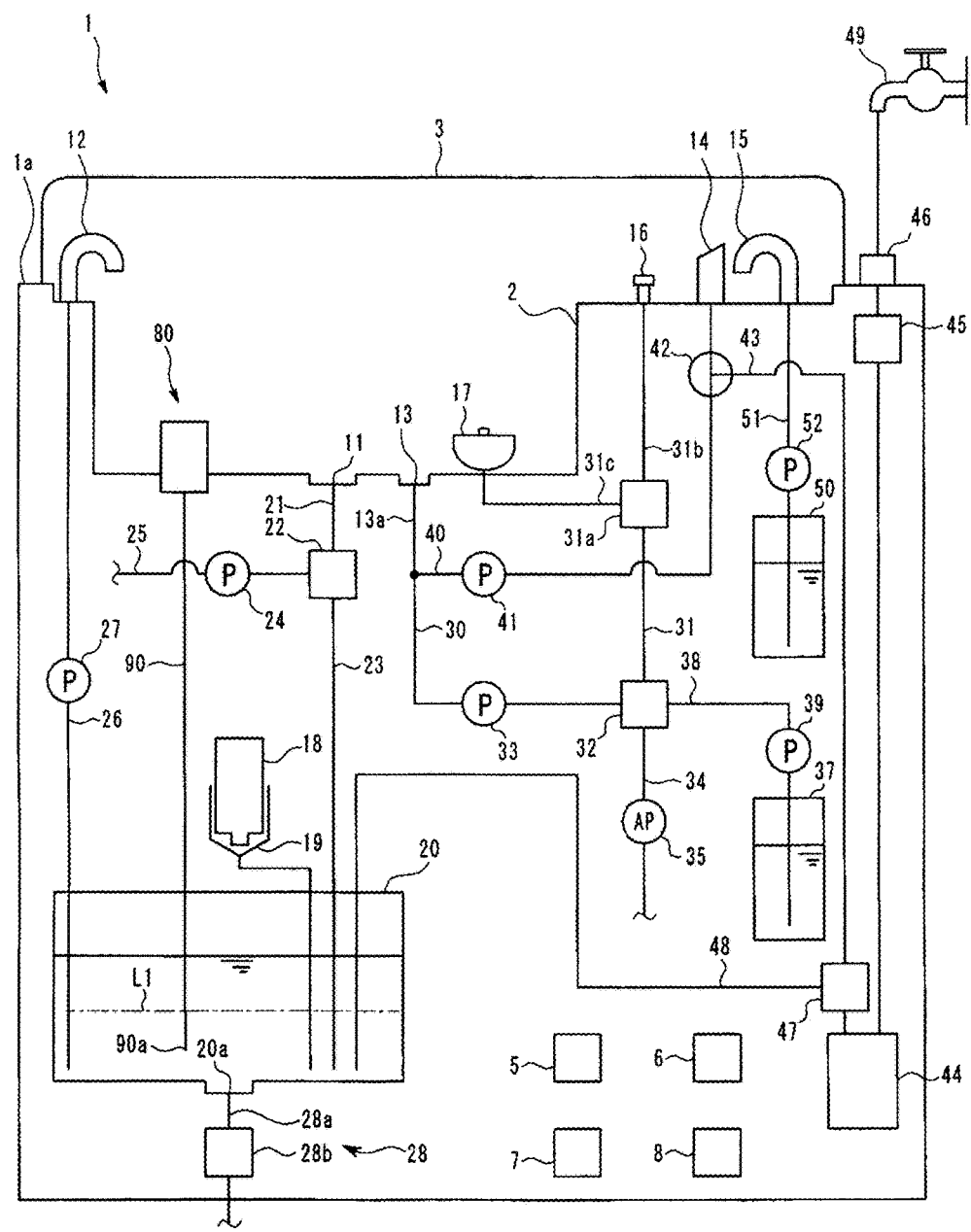
FIG. 12 is a diagram illustrating a configuration of the endoscope reprocessor of a second embodiment.
Figure 13:
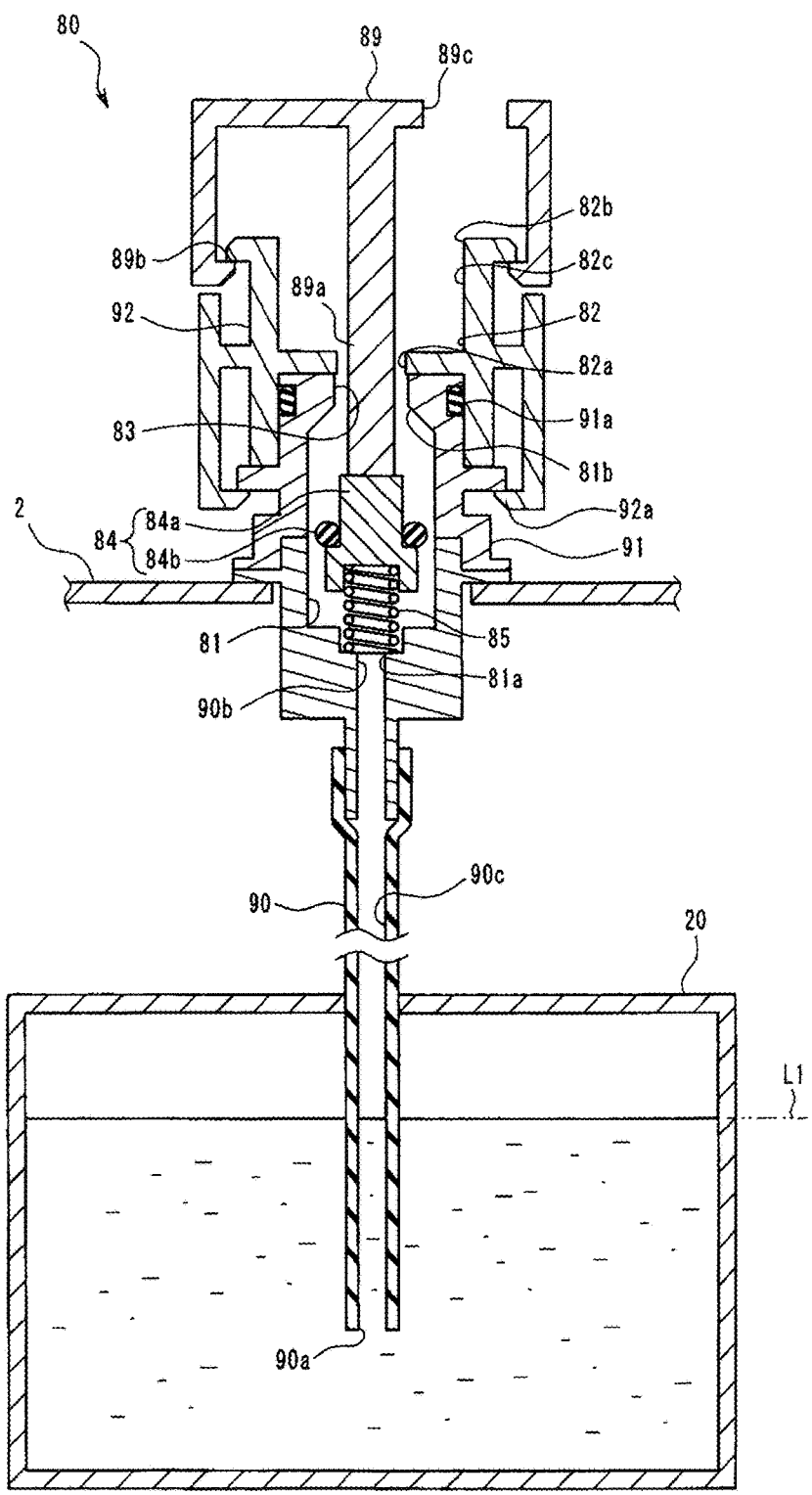
FIG. 13 is a sectional view illustrating a configuration of a plug opener of the second embodiment.

The endoscope reprocessor 1 of the present embodiment illustrated in FIG. 12 is different from the first embodiment in that the medicinal solution sampling portion 80 is arranged inside the treatment tank 2. In addition, the medicinal solution sampling portion 80 of the present embodiment illustrated in FIG. 13 is different from the first embodiment in the configuration of the plug opener 89.

The base portion 91 of the medicinal solution sampling portion 80 is fixed to the bottom surface of the treatment tank 2 for example. Therefore, in the case that the plunger 86 is taken out from the inside of the second chamber 82, the inside of the second chamber 82 is opened inside the treatment tank 2. Therefore, in the present embodiment, by executing the reprocessing treatment of the endoscope inside the treatment tank 2, treatment similar to the reprocessing treatment can be executed to the inside of the second chamber 82 as well. The operation of sampling and returning the medicinal solution inside the medicinal solution storage portion 20 by the medicinal solution sampling portion 80 is similar to that of the first embodiment.

The plug opener 89 of the present embodiment includes a pressurizing portion 89a which can be inserted into the constricted portion 83, a locking portion 89b configured to hold the pressurizing portion 89a at a predetermined position to the first chamber 81, and a fluid transmitting portion 89c which is a gap that transmits the fluid from the inside of the treatment tank 2 to the constricted portion 83 and the first chamber 81.

The locking portion 89b attachably and detachably engages with the base portion 91 or the cylinder portion 92. The locking portion 89b is connected to the pressurizing portion 89a, and in the state of engaging with the base portion 91 or the cylinder portion 92, holds the pressurizing portion 89a at a position of pressing down the first advancing/retreating portion 84 to the second position. In addition, the fluid transmitting portion 89c includes an opening that allows the traffic of the fluid between the inside of the treatment tank 2 and the constricted portion 83 in the state that the locking portion 89b engages with the base portion 91 or the cylinder portion 92.

Therefore, by the locking portion 89b of the plug opener 89 engaging with the base portion 91 or the cylinder portion 92, the passage 90c of the sampling tube 90 of the medicinal solution sampling portion 80 and the first chamber 81 are turned to the state of being communicated with the inside of the treatment tank 2, and the liquid introduced into the treatment tank 2 passes through the constricted portion 83, the first chamber 81 and the sampling tube 90 and flows into the medicinal solution storage portion 20 by gravity.

In the endoscope reprocessor 1 of the present embodiment, for example, in the case of executing the operation of diluting the stock solution of the medicinal solution supplied from the medicinal solution bottle 18 into the medicinal solution storage portion 20 with the water, the locking portion 89b of the plug opener 89 is made to engage with the base portion 91 or the cylinder portion 92.

Thereafter, by turning the three-way valve 42 to the state of communicating the circulation nozzle 14 and the water supply conduit 43, turning the dilution valve 47 to the state of communicating the water filter 44 and the three-way valve 42, and turning the water introducing valve 45 to the open state, the water supplied from the water supply source 49 is introduced from the circulation nozzle 14 to the inside of the treatment tank 2. The water introduced to the inside of the treatment tank 2 is introduced to the inside of the medicinal solution storage portion 20 through the constricted portion 83 of the medicinal solution sampling portion 80, the first chamber 81 and the sampling tube 90, and dilutes the stock solution of the medicinal solution. After a predetermined amount of the water is introduced to the inside of the medicinal solution storage portion 20, the water introducing valve 45 is turned to the closed state, and the plug opener 89 is detached from the medicinal solution sampling portion 80.

In this way, in the present embodiment, by making the water flow into the medicinal solution sampling portion 80 when diluting the stock solution of the medicinal solution, the liquid such as the medicinal solution that remains inside the medicinal solution sampling portion 80 can be made to flow out. By making the liquid such as the medicinal solution that remains inside the medicinal solution sampling portion 80 flow out, the remaining liquid is prevented from being mixed in the sampled medicinal solution when the medicinal solution is sampled by the medicinal solution sampling portion 80 next time, and medicinal effect confirmation test can be accurately executed.

Note that, after the stock solution of the medicinal solution is diluted inside the medicinal solution storage portion 20, by keeping the plug opener 89 attached to the medicinal solution sampling portion 80 and operating the medicinal solution pump 27 to introduce the medicinal solution inside the medicinal solution storage portion 20 to the inside of the treatment tank 2, the operation of making the medicinal solution flow to return to the inside of the medicinal solution storage portion 20 through the constricted portion 83, the first chamber 81 and the sampling tube 90 may be executed further.

In this way, by circulating the newly diluted medicinal solution between the medicinal solution storage portion 20 and the treatment tank 2 through the constricted portion 83, the first chamber 81 and the sampling tube 90, mixing of the stock solution of the medicinal solution and the water can be executed, and the water remaining inside the medicinal solution sampling portion 80 can be made to flow out. Prior to medicinal solution sampling by the medicinal solution sampling portion 80, by making the newly diluted unused medicinal solution flow into the medicinal solution sampling portion 80, the medicinal effect confirmation test can be accurately executed.

Note that, in the case of circulating the medicinal solution between the medicinal solution storage portion 20 and the treatment tank 2 through the constricted portion 83, the first chamber 81 and the sampling tube 90, in order to increase a flow rate of the medicinal solution and accelerating the mixing, it is preferable to circulate the medicinal solution through the drainage port 11, the discharge conduit 21 and the collection conduit 23 further.

After the operation of making the medicinal solution flow between the medicinal solution storage portion 20 and the treatment tank 2 and performing the mixing ends, the plug opener 89 is detached from the medicinal solution sampling portion 80.

As described above, the endoscope reprocessor 1 of the present embodiment rinses the inside of the medicinal solution sampling portion 80 with the water or the medicinal solution, and can prevent the old medicinal solution from remaining inside the medicinal solution sampling portion 80.

Note that the present invention is not limited to the above-described embodiments, and can be appropriately modified without opposing the gist or idea of the invention read from the scope of claims and the entire description, and the endoscope reprocessor accompanied by such a modification is also included in the technical scope of the present invention.

According to the present invention, the endoscope reprocessor that facilitates sampling of the medicinal solution from the medical solution storage portion and the return of the sampled medicinal solution to the medicinal solution storage portion can be realized.

What is claimed is:

1. An endoscope reprocessor comprising:
a medicinal solution storage portion configured to store a medicinal solution;
a sampling tube including a first end portion opened at or below a predetermined water level inside the medicinal solution storage portion, and a second end portion opened at a position higher than the predetermined water level, the second end portion being outside the medicinal solution storage portion;
a first chamber including a first opening and a second opening, the first opening communicating with, the second end portion of the sampling tube;
a second chamber having an opening portion and a communication port connectable to the second opening of the first chamber;
a constricted portion provided in the second opening of the first chamber, the constricted portion being provided with an inner diameter smaller than an inner diameter of the first chamber;
a moving portion configured to advance and retreat inside the first chamber between a first position to block the second opening and a second position to open the second opening, the second position being farther away from the second opening than the first position;
an energizing portion that energizes the moving portion in a direction from the second position to the first position; and
a retention portion arranged at one of the constricted portion or the first moving portion, the retention portion being configured to be in close contact with one of an inner surface of the second opening or with an inner surface of the first chamber when the moving portion is at the first position.

2. The endoscope reprocessor according to claim 1, wherein the moving portion includes an advancing portion configured to advance into the constricted portion when the moving portion is positioned at the first position.

3. The endoscope reprocessor according to claim 2, wherein the retention portion is an elastic portion arranged on an inner periphery of the constricted portion or an outer periphery of the advancing portion, the retention portion being provided with elasticity.

4. The endoscope reprocessor according to claim 1,
wherein the first chamber is provided at a base portion fixed to the endoscope reprocessor, and
the second chamber is provided at a member that is attachable to and detachable from the base portion.

5. The endoscope reprocessor according to claim 2, further comprising
a plunger including:
a piston portion configured to advance and retreat inside the second chamber while an outer periphery is in airtight contact with an inner peripheral surface of the second chamber; and
a holding portion connected to the piston portion, the holding portion being inserted to the communication port to be in contact with the moving portion when the piston portion is in the second chamber, to thereby hold a position of the moving portion,
wherein the plunger is attachable to and detachable from the second chamber through the opening portion.

6. The endoscope reprocessor according to claim 5, wherein, when the moving portion held by the holding portion is at the first position,
the piston portion is out of the second chamber.

7. The endoscope reprocessor according to claim 6, wherein, when the moving portion held by the holding portion is at the second position and the piston portion is in airtight contact with the inner peripheral surface of the second chamber,
the advancing portion is out of the constricted portion.

8. The endoscope reprocessor according to claim 1, further comprising an inspection port formed in the second chamber between the opening portion and the communication port.

* * * * *